US011529367B2

(12) United States Patent
Aoki et al.

(10) Patent No.: US 11,529,367 B2
(45) Date of Patent: Dec. 20, 2022

(54) RADIATION DAMAGE PROTECTIVE AGENT (71) Applicants: MiZ Company Limited, Kanagawa (JP); Incorporated Medical Institution YUKOKAI, Tokyo (JP)

(72) Inventors: Yukimasa Aoki, Tokyo (JP); Shinichi Hirano, Kanagawa (JP); Bunpei Sato, Kanagawa (JP); Ryosuke Kurokawa, Kanagawa (JP)

(73) Assignees: MIZ COMPANY LIMITED, Kanagawa (JP); INCORPORATED MEDICAL INSTITUTION YUKOKAI, Tokyo (JP)

( * ) Notice: Subject to any disclaimer, the term of this patent is extended or adjusted under 35 U.S.C. 154(b) by 0 days.

(21) Appl. No.: 16/465,567

(22) PCT Filed: Dec. 26, 2017

(86) PCT No.: PCT/JP2017/046633
§ 371 (c)(1),
(2) Date: May 30, 2019

(87) PCT Pub. No.: WO2018/124067
PCT Pub. Date: Jul. 5, 2018

(65) Prior Publication Data
US 2019/0282611 A1 Sep. 19, 2019

(30) Foreign Application Priority Data

Dec. 27, 2016 (JP) .............................. JP2016-252753
Nov. 30, 2017 (JP) .............................. JP2017-231072

(51) Int. Cl.
| A61K 33/00 | (2006.01) |
| A61P 39/06 | (2006.01) |
| A61K 9/00 | (2006.01) |
| A61P 7/00 | (2006.01) |
| A61G 10/02 | (2006.01) |
| A61H 33/14 | (2006.01) |
| A61M 16/12 | (2006.01) |
| A61N 5/10 | (2006.01) |
| A61P 35/00 | (2006.01) |

(52) U.S. Cl.
CPC .............. *A61K 33/00* (2013.01); *A61G 10/02* (2013.01); *A61G 10/023* (2013.01); *A61H 33/14* (2013.01); *A61K 9/007* (2013.01); *A61M 16/12* (2013.01); *A61N 5/10* (2013.01); *A61P 7/00* (2018.01); *A61P 35/00* (2018.01); *A61P 39/06* (2018.01); *A61H 2033/148* (2013.01); *A61N 2005/1094* (2013.01)

(58) Field of Classification Search
CPC ...................... A61K 33/14; A61K 33/148
See application file for complete search history.

(56) References Cited

U.S. PATENT DOCUMENTS

| 9,050,278 B2 * | 6/2015 | Ohta ........................ A61P 9/10 |
| 11,026,967 B2 | 6/2021 | Ideka et al. |
| 11,033,574 B2 | 6/2021 | Sato et al. |
| 2010/0006099 A1 | 1/2010 | Murota |
| 2013/0296768 A1 * | 11/2013 | Joshi ..................... A61M 35/30 |
| | | 604/23 |
| 2019/0388462 A1 | 12/2019 | Satoh et al. |

FOREIGN PATENT DOCUMENTS

| EP | 2067463 | 6/2009 |
| JP | 2011-207841 | 10/2011 |
| JP | 6133526 B1 | 5/2017 |
| WO | WO-2008/013163 A1 | 1/2008 |
| WO | WO-2014/017046 | 1/2014 |
| WO | WO-2014/024984 A1 | 2/2014 |
| WO | WO-2014/077358 | 5/2014 |

OTHER PUBLICATIONS

Ichihara, M. et al. "Beneficial biological effects and the underlying mechanisms of molecular hydrogen-comprehensive review of 321 original articles", Medical Gas Research 2015, 5:12 (Year: 2015).*
Shimouchi, A. et al. "Molecular hydrogen consumption in the human body during the inhalation of hydrogen gas", Oxygen Transport to tissue XXXV, 2013, 789:315-321. (Year: 2013).*
Zhao, S et al. "Therapeutic effects of hydrogen-rich solution on aplastic anemia in vivo", Cell Physiol Biochem 2013;32:5499-560. (Year: 2013).*
Chuai, Y. et al. "A possible prevention strategy of radiation pneumonitis: Combine radiotherapy with aerosol inhalation of hydrogen-rich solution", Med. Sci. Monit, 2011; 17 (4) HY1-4. (Year: 2011).*
Chuai, Y. et al., "Hydrogen-rich saline attenuates radiation-induced male germ cell loss in mice through reducing hydroxyl radicals" Biochem. J. 2012, 44249-56.*
Farese et al., "Leridistim, a Chimeric Dual G-CSF and IL-3 Receptor Agonist, Enhances Multilineage Hematopoietic Recovery in a Nonhuman Primate Model of Radiation-Induced Myelosuppression: Effect of Schedule, Dose, and Route of Administration," Stem Cells, 19(6): 522-33 (2001).
Guo et al., "Protective Effectis of Hydrogen against Low-Dose Long-Term Radiation-Induced Damage to the Behavioral Performances, Hematopoietic System, Genital System, and Splenic Lymphocytes in Mice", Oxidative Medicine and Cellular Longevity, vol. 2016, pp. 1-15 (2016).

(Continued)

Primary Examiner — Gina C Justice
(74) Attorney, Agent, or Firm — Crowell & Moring LLP (57) ABSTRACT The present application provides a radiation damage protecting agent comprising hydrogen gas as an active ingredient at a concentration of 18.5% by volume or less, for treating or alleviating, in a hyperbaric capsule under a pressure higher than standard atmospheric pressure, radiation damage in a human patient who has been exposed to radiation or who has received or receives radiotherapy, and a hyperbaric capsule for administering a hydrogen gas-containing therapeutic agent such as the radiation damage protecting agent to a patient including a human.

4 Claims, 9 Drawing Sheets (56) References Cited

OTHER PUBLICATIONS

Chuai et al., Hydrogen-rich Saline Protects Spermatogenesis and Hematopoiesis in Irradiated BALB/c Mice, *Med. Sci. Monit.*, 18:BR89-94 (2012).
Kang et al., Effects of drinking hydrogen-rich water on the quality of life of patients treated with radiotherapy for liver tumors, *Med. Gas Res.*, 1:11 (2011).
Terasaki et al., Hydrogen Therapy Attenuates Irradiation-Induced Lung Damage by Reducing Oxidative Stress, *Am. J. Physiol. Lung Cell. Mol . . . Physiol.*, 304(4):L415-26 (Jul. 2011).
Wantanabe, Summary of Doctoral Thesis, Study on Protection Effect of 1.3% Hydrogen Gas Using Radiation Dermatitis Rat Model, National Institution of Academic Degrees and Quality Enhancement of Higher Educaiton (JP), 37 (Feb. 2016).

\* cited by examiner

RADIATION DAMAGE PROTECTIVE AGENT

RELATED APPLICATIONS

The present patent document is a § 371 filing based on PCT Application Serial No. PCT/JP2017/046633, filed Dec. 26, 2017, which claims priority to Japanese Patent Application Nos. JP 2016-252753, filed Dec. 27, 2016 and JP 2017-231072, filed Nov. 30, 2017, which are hereby incorporated by

TECHNICAL FIELD

The present invention relates to a radiation damage protecting agent useful for treating or alleviating radiation damage caused by radiation exposure or radiotherapy.

BACKGROUND ART

Workers in nuclear power plants, clinical laboratory technicians dealing with radioactive test agents, doctors and radiological technicians engaged in X-ray examination and cancer radiation treatment and others are always exposed to a small amount of radiation during work. Also, nuclear power plant accidents may cause the workers as well as residents in the surrounding areas to be exposed to radiation. Depending on the amount of radiation exposure, the hematopoietic system, immune system, digestive system, respiratory system, central nervous system and the like may be damaged, and if the exposure dose exceeds the lethal dose, it may lead to death.

Further, recent statistics have suggested that, in our country (Japan), one in two persons suffers from cancer and one in three persons dies from cancer in his or her life. Examples of the major treatments for cancer include three treatments, that is, surgery, radiotherapy, and chemotherapy using an anticancer agent. Among them, radiotherapy is an effective therapy for inhibiting proliferation of cancer cells by applying radiation to the cancer-affected area, but it not only damages the target cancer tissue, it also affects and damages the normal tissues present in the irradiation area.

In recent years, intensity-modulated radiation therapy (IMRT) using a device referred to as "TomoTherapy" is used to alleviate the above-described radiation damage. IMRT has the advantage that by using computer technology, the direction, position, intensity, irradiated range and irradiation time of radiation can be adjusted according to the complicated shape of the cancer lesion to irradiate a patient with the radiation, and can thereby reduce the irradiation dose to the normal tissues compared to conventional irradiation.

However, in fact, even if the radiation dose to the normal tissue is reduced in the patient by using IMRT, damage by radiation (adverse effects) cannot be avoided when the patient has multiple lesions and the tumor volume is large. The development of adverse effects is one of the limiting factors in IMRT irradiation. For this reason, hyperbaric therapy in which patients are placed under a hyperbaric environment after irradiation has been performed, but it has not led to a significant effect for alleviating the adverse effects. Also, radiation damage protecting agents such as L-cysteine, glutathione, SOD (superoxide dismutase), GM-CSF (granulocyte-macrophage colony stimulating factor), 5-aminolevulinic acid, romiplostim (thrombopoietin receptor agonist), nitroprusside and lactoferrin have been reported, but these also has not led to effective alleviation of radiation damage as well (Patent Literatures 1, 2 and 3).

It is known that molecular hydrogen does not react with a reactive oxygen species which plays an important role in living organisms, and it reacts selectively with a reactive oxygen species having particularly strong oxidizability and reactivity such as OH radicals, $O^{2-}$ radicals or $ONOO^{-}$ ions to detoxify them and exhibit an antioxidant effect. Recent studies mainly using animal models have reported that molecular hydrogen exhibits effects other than the antioxidant effect such as an anti-inflammatory effect, an anti-apoptotic effect, an anti-allergic effect, a lipid metabolism-improving effect and a signal transduction-regulating effect.

Regarding radiation damage, for example, it has been reported that as a result of examining the quality of life (QOL) of liver cancer patients, who received radiotherapy (total radiation dose of 50 to 60 Gy for 7 to 8 weeks), when drinking hydrogen-dissolved water, anorexia and taste disorder were improved, but nausea (vomiting) and diarrhea were similar to the control and the white blood cell count, red blood cell count and platelet count in blood also did not differ significantly from the control (Non Patent Literature 1). On the other hand, it has been reported that in an experiment in which hydrogen-dissolved water was fed to mice irradiated with $^{60}Co$ gamma rays (0.1 to 4.0 Gy), the number of endogenous hematopoietic splenic colony-forming cells, the number of bone marrow nucleated cells and the peripheral white blood cell count increased (Non Patent Literature 2). The inhibition mechanism of cancer cell proliferation by irradiation is a damage of cancer cells caused by a reactive oxygen species and free radical generated at the time of irradiation, but damages to the surrounding tissues as an adverse effect are inevitable. There is therefore a strong desire for a radiation damage protecting agent which is not reduced in its therapeutic effect of radiation but can alleviate only the adverse effects at the time of irradiation.

CITATION LIST

Patent Literature

[Patent Literature 1]
  International Publication No. WO 2014/017046
[Patent Literature 2]
  Japanese Patent Laid-Open No. 2011-207841
[Patent Literature 3]
  International Publication No. WO 2014/077358

Non Patent Literature

[Non Patent Literature 1]
  Kang K-M et al., Medical Gas Research 2011; 1: 11
[Non Patent Literature 2]
  Cauai Y et al., Med Sci Monit, 2012; 18: BR89-94

SUMMARY OF INVENTION

Technical Problem

An object of the present invention is to provide a radiation damage protecting agent which can alleviate or improve radiation damage such as bone marrow damage at the time of radiation exposure and radiotherapy and can be also expected to have the effect of improving inflammation and deterioration in immune function by radiation.

Solution to Problem

The present inventors have found that the above-described problems can be dissolved by a radiation damage protecting agent comprising hydrogen gas as an active ingredient, for treating, in a hyperbaric capsule, a human patient who has been exposed to radiation or who has received or receives radiotherapy, and as a result, have completed the prevent invention.

The present invention includes the following features:

(1) A radiation damage protecting agent comprising hydrogen gas as an active ingredient, for treating or alleviating, in a hyperbaric capsule under a pressure higher than standard atmospheric pressure, radiation damage in a human patient who has been exposed to radiation or who has received or receives radiotherapy.

(2) The radiation damage protecting agent according to (1) above, wherein the radiation damage is bone marrow damage.

(3) The radiation damage protecting agent according to (2) above, wherein the bone marrow damage is a decrease in the number of blood cells.

(4) The radiation damage protecting agent according to (1) or (2) above, wherein the radiation damage is damage caused by a reactive oxygen species.

(5) The radiation damage protecting agent according to any one of (1) to (4) above, wherein the hydrogen gas is comprised at a concentration of 0.5% by volume to 18.5% by volume.

(6) The radiation damage protecting agent according to (5) above, wherein the concentration of the hydrogen gas is 1% by volume to 10% by volume.

(7) The radiation damage protecting agent according to any one of (1) to (6) above, wherein the hyperbaric capsule contains air and is maintained under an atmospheric pressure in the range of higher than the standard atmospheric pressure and 7.0 atm or less.

(8) The radiation damage protecting agent according to any one of (1) to (7) above, wherein the hydrogen gas is administered transpulmonarily to the human patient.

(9) The radiation damage protecting agent according to any one of (1) to (8) above, wherein the human patient is a cancer patient.

(10) A hyperbaric capsule for administering the radiation damage protecting agent according to any one of (1) to (9) above to a human patient, comprising: a housing capable of housing the human patient who has been exposed to radiation or who has received or receives radiotherapy and capable of forming a sealed space; and a gas supply system for supplying the radiation damage protecting agent comprising hydrogen gas.

(11) A hyperbaric capsule comprising: a pressure-tight housing capable of housing a patient that receives hydrogen gas treatment and capable of forming a sealed space; and a gas supply system for supplying a disease-treating gas comprising hydrogen gas.

The radiation damage protecting agent comprising hydrogen gas as an active ingredient according to the present invention can treat, alleviate and improve radiation damage such as bone marrow damage in a human patient who has been exposed or is exposed to radiation or who has received or receives radiotherapy, and can be also expected to have the effect of improving inflammation and deterioration in immune function by further characteristics of the hydrogen gas that eliminates or scavenges a reactive oxygen species (ROS) caused by radiation or a disease such as a cancer.

This specification encompasses the contents disclosed in Japanese Patent Application No. 2016-252753 (filing date: Dec. 27, 2016) and Japanese Patent Application No. 2017-231072 (filing date: Nov. 30, 2017), from which the present application claims priority.

DESCRIPTION OF EMBODIMENTS

The present invention will be described in more detail.

1. Radiation Damage Protecting Agent

According to the first aspect of the present invention, a radiation damage protecting agent comprising hydrogen gas as an active ingredient, for treating or alleviating, in a hyperbaric capsule under a pressure higher than the standard atmospheric pressure, radiation damage in a human patient who has been exposed to radiation or who has received or receives radiotherapy is provided.

As used herein, the term "radiation damage protecting agent" refers to a pharmaceutical or pharmaceutical composition for treating, alleviating or inhibiting the radiation damage in a human patient who has subjected or is subjected to the radiation damage by radiation exposure or radiotherapy. Herein, the phrase "a human patient who has been subjected or is subjected to the radiation damage" refers to a human patient which was exposed to radiation so that he (she) became damaged, or both a human patient after receiving radiation treatment and a human patient before receiving the radiation treatment in radiotherapy. By administering the radiation damage protecting agent before radiotherapy, it is possible preventively inhibit the influence of radiation damage, but it is desirable not to reduce the effect of the radiation treatment, and it is preferable to administer the radiation damage protecting agent again after the radiation treatment.

According to the present invention, the radiation damage protecting agent comprises a "hydrogen gas" as an active ingredient. A hydrogen gas-containing gas is usually used. The hydrogen gas-containing gas is specifically air containing hydrogen gas or a mixed gas containing hydrogen gas and oxygen gas. Examples of the concentration of hydrogen gas in the hydrogen gas-containing gas include, but not limited to, 18.5% by volume or less such as 0.5% by volume to 18.5% by volume, preferably 1% by volume to 10% by volume such as 2% by volume to 6% by volume or 3% by volume to 6% by volume, and more preferably 4% by volume to 6% by volume such as 4% by volume to 5% by volume. When the gas other than hydrogen gas is air, the concentration of air is for example in the range of 81.5% by volume to 99.5% by volume, and when the gas other than hydrogen is an oxygen gas-containing gas, the concentration of oxygen gas is for example in the range of 21% by volume to 99.5% by volume. The nitrogen gas can be included in the hydrogen gas-containing gas as the other main gas, and a gas contained in air such as carbon dioxide may be further included in the amount approximately equal to its amount contained in air. In any event, since hydrogen is a flammable and explosive gas, hydrogen should be included in a composition at a level safe for a subject such as a human to be administered to the subject.

It is preferable to produce the hydrogen gas, preferably using a small-sized hydrogen gas supply device, so as to be usable in a hyperbaric capsule in which the hydrogen gas can be produced at a safe level and mixed with a predetermined amount of air or oxygen.

Examples of the hydrogen gas supply device include, but not limited to, a hydrogen gas supply device in which the hydrogen gas generated by reaction between water and a hydrogen-generating agent (such as metal aluminum) can be mixed with a dilution gas (such as air or oxygen) at a predetermined ratio (Japanese Patent No. 5228142), and a hydrogen gas supply device in which the hydrogen gas generated by utilizing electrolysis of water is mixed with a dilution gas (Japanese Patent No. 5502973, Japanese Patent No. 5900688 and the like). By using the device, it is possible to prepare a hydrogen gas-containing gas having a hydrogen concentration of 0.5% by volume to 18.5% by volume, for example.

As used herein, the phrase "a human patient who has been exposed to radiation or who has received radiotherapy" refers to, but not limited to, for example, workers in nuclear power plants, researchers or engineers in radiation research/experiment facilities, clinical laboratory technicians dealing with radioactive test agents, doctors and radiological technicians engaged in X-ray examination and cancer radiation treatment, patients who have received radiation treatment or radiation examination (such as cancer patients), and others.

For example, radiotherapy, when performed in a cancer patient, destroys or regress cancer cells or cancer tissues by irradiating the cancer-affected area of the patient with radiation such as X-rays, gamma rays, electron beams, heavy particle beams or proton beams. However, on the other hand, it often generates, in the patient, adverse effects and sequelae due to irradiation such as nausea (vomiting), diarrhea, hair loss, anorexia, malaise, drymouth, dermatitis, pneumonia and enteritis, which are caused by radiation damage such as damage of normal tissues of the patient by radiation or bone marrow damage (such as bone marrow depression) in the patient by radiation, which damages the bone marrow tissue and causes a decrease in blood cells.

Radiation damage is a physical damage caused by exposure to radiation, in which it is known that DNAs are generally damaged and that when the damaged DNAs are not repaired, cell death and canceration of cells are caused. The physical damage includes the above-mentioned adverse effects and sequelae. Although the extent of the damage differs depending on the exposure dose, it is believed that the radiation damage protecting agent of the present invention will be effective against the damage by the exposure dose of 1.5 Gy or less at an early stage immediately after exposure.

The bone marrow damage is a decrease in blood cells (a blood cell count) such as a white blood cell count, a platelet count or a red blood cell. The extent of damage varies depending on the type of radiation, irradiation range, irradiation dose, patient's condition (severity) and therapy.

White blood cells, which are immunocompetent cells, include lymphocytes, granulocytes and monocytes and act to protect against foreign substances invading the body from the outside. The total number of white blood cells in an adult is 5000 to 8000 per $mm^3$ of blood, but it may be decreased to approximately 20% by radiotherapy.

Platelets act to stop bleeding due to platelet aggregation when the blood vessel walls are damaged. The normal range of platelet count in an adult is 140,000 to 340,000/μL blood, but it may be decreased to approximately 40% by radiotherapy.

Red blood cells act to carry oxygen to the whole body and carry carbon dioxide to the lungs. The normal range of red blood cell count in an adult is 3,900,000 to 5,700,000/μL blood. Red blood cells are not decreased immediately by radiotherapy due to their long lifetime, but if they fall below the lower limit of the normal range, anemia appears in approximately 1 to 2 weeks after the start of radiotherapy.

By administering the radiation damage protecting agent of the present invention to the patient, it is possible to eliminate, alleviate or inhibit radiation damage such as bone marrow damage. In the Example below, administration of the radiation damage protecting agent to a cancer patient after subjected to IMRT made the red blood cell count to be within the normal range and decreases in the white blood cell count and platelet count to be statistically significantly inhibited.

Another example of radiation damage is a damage caused by a reactive oxygen species. When irradiating a patient with radiation, it is known that a reactive oxygen species such as an OH radical, an $O^{2-}$ radical, $H_2O_2$ or an $ONOO^-$ ion generated by decomposition of a water molecule or the like in the body cause the oxidative stress which in turn causes inflammation in cells and tissues and thereby causes various diseases (such as inflammation or deterioration in immune function).

The radiation damage protecting agent of the present invention can eliminate, scavenge or decrease a reactive oxygen species by reacting with such a reactive oxygen species, and therefore is also effective in improving inflammation and a deterioration in immune function.

One of further features of the present invention is to administer the above-described radiation damage protecting agent to the above-described human patient in a hyperbaric capsule.

Among literatures described in the Background Art above, Non Patent Literature 1 is to be noted. This Literature has reported that as a result of examining the quality of life (QOL) of human liver cancer patients, who received radiotherapy (total radiation dose of 50 to 60 Gy for 7 to 8 weeks), when drinking "hydrogen-dissolved water", anorexia and taste disorder were improved, vomiting and diarrhea were similar to the control, and the white blood cell count, red blood cell count and platelet count in blood also did not differ significantly from the control. On the other hand, in the present invention, air mixed with hydrogen gas (at a concentration of 4% by volume to 6% by volume in Example 1 below) was administered transpulmonarily by inhalation to a human cancer patient in a hyperbaric capsule under a pressure higher than the standard atmospheric pressure (adjusted to 1.35 atm by taking in air in Example 1 below), and as a result, decreases in the white blood cell count and platelet count in peripheral blood were significantly inhibited (See FIGS. 3 and 7).

In comparison of the present invention with Non Patent Literature 1, they are obviously different in the administration conditions including the dosage form and administration method from each other. Importantly, the radiation damage protecting agent of the present invention is to be administered on the conditions characterized in that a therapeutically effective amount of hydrogen gas is administered transpulmonarily to a human patient who has been exposed or has received or receives radiotherapy in a hyperbaric capsule under a pressure higher than the standard atmospheric pressure.

In an embodiment of the present invention, the hyperbaric capsule contains air and is maintained under an atmospheric pressure in the range of higher than the standard atmospheric pressure (representing approximately 1.013 atm) and 7.0 atm or less, preferably in the range of higher than the standard atmospheric pressure and 5.0 atm or less, more preferably in the range of higher than the standard atmospheric pressure and 1.4 atm or less, and further preferably in the range of higher than the standard atmospheric pressure and 1.35 atm or less.

In another embodiment of the present invention, the radiation damage protecting agent comprising hydrogen gas is administered transpulmonarily to the above-described human patient. The radiation damage protecting agent is delivered systemically from the lung by inhaling or taking in it through the oral or nasal cavity of the patient. The hydrogen molecule (gas) which is an active ingredient in the radiation damage protecting agent of the present invention is the smallest among the molecules, and can therefore penetrate through the blood vessel wall and alleviate or inhibit, at an early stage, inflammation and the like caused by the oxidative stress in organs and tissues such as blood vessels damaged by radiation. In that context, it is also possible to use the radiation damage protecting agent of the present invention for emergency care for a patient exposed to radiation.

The radiation damage protecting agent of the present invention is administered once to three times a day, preferably once a day, for 10 minutes to 60 minutes or more, preferably 20 minutes to 40 minutes, for example 30 minutes per administration, and can be administered over a period of 1 week to 6 months or more, preferably 2 weeks to 3 months, depending on the extent of recovery from radiation damage in a patient.

2. Hyperbaric Capsule

According to the second aspect, the present invention provides a hyperbaric capsule for administering the above-described radiation damage protecting agent to a human patient, comprising: a housing capable of housing the human patient who has been exposed to radiation or who has received or receives radiotherapy and capable of forming a sealed space; and a gas supply system for supplying the radiation damage protecting agent comprising hydrogen gas.

According to the third aspect, the present invention further provides a hyperbaric capsule comprising: a pressure-tight housing capable of housing a patient that receives hydrogen gas treatment and capable of forming a sealed space; and a gas supply system for supplying a disease-treating gas comprising hydrogen gas. This hyperbaric capsule can be used for the prevention, treatment, alleviation and the like of a patient (in this case, the "patient" refers to mammals including a human) with any disease that can be treated with hydrogen gas, in addition to the human patient who has been exposed to radiation or who has received or receives radiotherapy.

The housing is designed so as to have sufficient strength to withstand an atmospheric pressure higher than the standard atmospheric pressure (approximately 1.013 atm) and 7.0 atm or less. The housing is also characterized that: it has a chamber space; it is preferably not angled as a whole but rounded so as to be pressure-resistant; it has a size capable of housing approximately 2 or 3 persons including a patient and a simple bed in which treatment can be performed; and it may be vertical or horizontal. Furthermore, the housing may be provided with casters or wheels so as to be carried for treatment in a desired place. The housing is preferably made of a lightweight material having high strength such as a reinforced plastic, a carbon fiber composite material, a titanium alloy or an aluminum alloy.

The housing comprises: a door capable of maintaining an airtight state so that air can be introduced thereinto to obtain a high atmospheric pressure; on its side surface, an air inlet and an air outlet for returning the atmospheric pressure to the normal pressure, and if desired, an exhaust valve; and further outside the housing, an air injector for air feeding such as an air compressor. Also, when providing, outside the housing, a gas generator of the gas supply system for supplying a disease-treating gas comprising hydrogen gas such as the radiation damage protecting agent, the housing can include a gas supply port and a pressure-resistant gas pipe (made of such a material as stainless steel or polyethylene) extending from the gas supply port to the patient. The housing can be provided with a flowmeter or a pressure gage at or near each of the air inlet and the gas supply port, and can be also provided with a flow controller. In addition, the housing may include a sensor and a meter for measuring and displaying the gas concentration of hydrogen gas, oxygen gas and the like, and an alarm for informing that the hydrogen concentration fall within a dangerous region.

The gas supply system for supplying a disease-treating gas comprising hydrogen gas such as the radiation damage protecting agent comprising hydrogen gas together with oxygen gas or air can include a gas generator, a gas introduction pipe, a flow controller, a flowmeter or a pressure gauge, and a mask worn by the patient to cover his/her mouth and nose for inhalation. The gas supply system can be also provided inside the housing. In this case, the gas generator can be placed at a predetermined position inside the housing to deliver a disease-treating gas containing hydrogen gas such as the radiation damage protecting agent generated by this gas generator to the patient, while adjusting the disease-treating gas, for example, by using a flow controller, a flowmeter or a pressure gauge, a hydrogen densitometer or the like with which the gas generator is provided.

EXAMPLE

The present invention will be described in more detail with reference to an example thereof, but the scope of the present invention will not be limited to the example.

[Example 1] Effect of Inhalation of Hydrogen Gas in Hyperbaric Capsule for Cancer Patient Who has Received Radiotherapy <Test Method>

The cancer patients who had visited Incorporated Medical Association YUKOKAI Clinic C4 (Director Koichi Aoki, (formerly) 618-1 Hongo-cho, Funabashi-shi, Chiba-ken 273-0033, Japan; (presently) 33-12 Motoyoyogi-cho, Shibuya-ku, Tokyo 151-0062, Japan) from May 2015 until November 2016 for the treatment of terminal cancer was subjected to testing. These patients were subjected to IMRT irradiation integrated with a computed tomograph (CT). Irradiation was in principle performed on a schedule of once a day, five times per week, and this schedule was repeated. Radiation was applied at 1 to 5 locations for 5 to 20 minutes once, and the number of times irradiation was performed was 5 to 20.

Among the above-mentioned patients, seven patients (3 males and 4 females) randomly sampled from patients who had visited from May 2015 to January 2016 were included in the control group. These patients were housed in a hyperbaric capsule (APF 2, 700×1900 mm; oxygen concentration: 28% by volume; Air Press Co., Ltd.) at 1.35 atm for 30 minutes after each irradiation with radiation to alleviate the adverse effects.

In addition, 16 patients (8 males and 8 females) who had visited from April 2016 until November 2016 were included in the hydrogen group. These patients were housed in the capsule similar to the above-mentioned capsule except that a hydrogen gas inhaler (MHG-44280, MiZ Company Limited), which generates approximately 6.5% by volume of hydrogen gas (4 L/min) by electrolysis of water, was connected in series with and upstream the air intake of the pressurizing device for the hyperbaric capsule provided outside the capsule, so as to feed high-pressure air containing hydrogen gas into the capsule, while the patients were allowed to inhale, via the nasal cannula, for 30 minutes, 4% by volume to 6% by volume of hydrogen gas (4 L/min) carried through a Y-shaped tube by which the air outlets of two hydrogen gas inhalers (MHG-2070 and MHG-2140, MiZ Company Limited) provided in the capsule were connected in parallel. The hydrogen gas concentration in the ceiling portion of the capsule was approximately 0.2% by volume.

Blood samples were taken periodically from both groups of patients before, during and after radiation treatment. The analysis items of blood were the white blood cell count (WBC), red blood cell count (RBC), hemoglobin level (Hb), hematocrit level (Ht) and platelet count (PLT), and these were used as indicators for hematopoietic function.

<Test Results>

Figure 1:
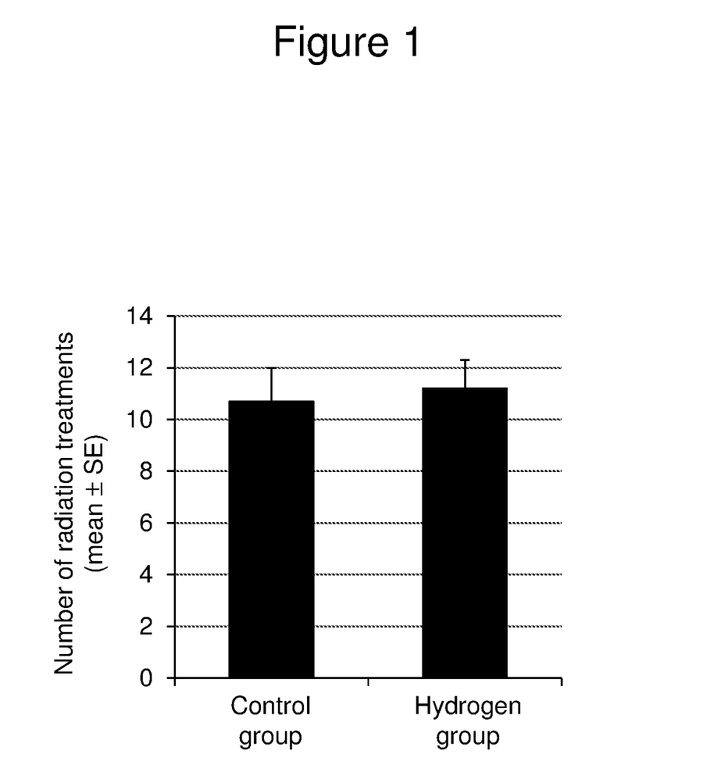
FIG. 1 is a graph showing the mean±standard error (SE) of the number of radiation treatments in the control group (Control, n=7) and the hydrogen group (H2, n=16), respectively.

FIG. 1 shows the mean±standard error (SE) of the number of radiation treatments in the control group (Control, n=7) and the hydrogen group (H2, n=16), respectively. The mean number of radiation treatments was 10.7±1.3 in the control group and 11.2±1.1 in the hydrogen group. There was no statistically significant difference between both groups, and the number of radiation treatments was almost the same in both groups in this test.

Figure 2:
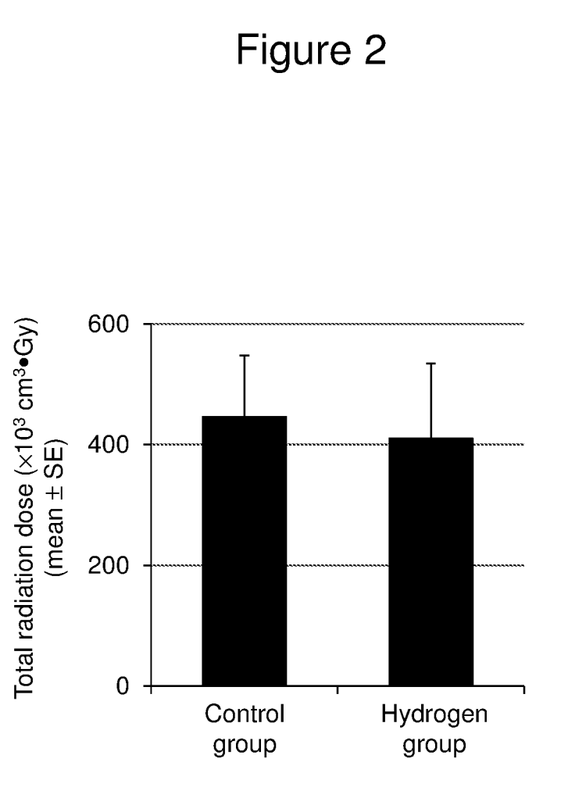
FIG. 2 is a graph showing the mean±standard error (SE) of the total radiation dose ($\times 10^3$ cm$^3$·Gy) determined by multiplying the volume of the irradiation site by the total dose of the radiation received during the period of radiation treatment in the control group (Control, n=7) and the hydrogen group (H2, n=16), respectively.

FIG. 2 shows the mean±standard error (SE) of the total radiation dose ($\times 10^3$ $cm^3 \cdot Gy$) determined by multiplying the volume of the irradiation site by the total dose of the radiation received during the period of radiation treatment in the control group (Control, n=7) and the hydrogen group (H2, n=16), respectively. The radiation dose was 446.0±101.8 in the control group and 410.2±124.4 in the hydrogen group. There was no statistically significant difference between both groups, and the total radiation dose was almost the same in both groups.

Figure 3:
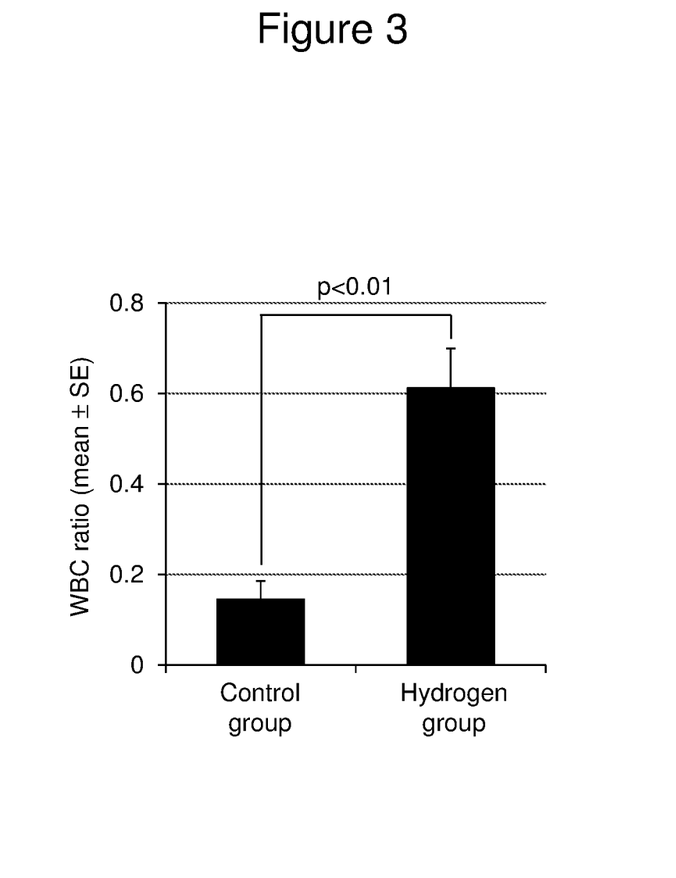
FIG. 3 is a graph showing the mean±standard error (SE) of the relative value of the white blood cell count (WBC) immediately after radiation treatment to the WBC before radiation treatment (the WBC before radiation treatment is taken as 1) in the control group (Control, n=7) and the hydrogen group (H2, n=16), respectively. All ratios are represented by the relative value of the WBC after radiation treatment to the WBC before radiation treatment.

FIG. 3 shows the mean±standard error (SE) of the relative value of the white blood cell count (WBC) immediately after radiation treatment to the WBC before radiation treatment (the WBC before radiation treatment is taken as 1) in the control group (Control, n=7) and the hydrogen group (H2, n=16), respectively. The WBC ratio was 0.145±0.041 in the control group and 0.612±0.088 in the hydrogen group. The decrease in the WBC ratio induced by radiation was significantly inhibited in the hydrogen group, compared with that in the control group, and a statistically significant difference ($p<0.01$) was observed between both groups.

Figure 4:
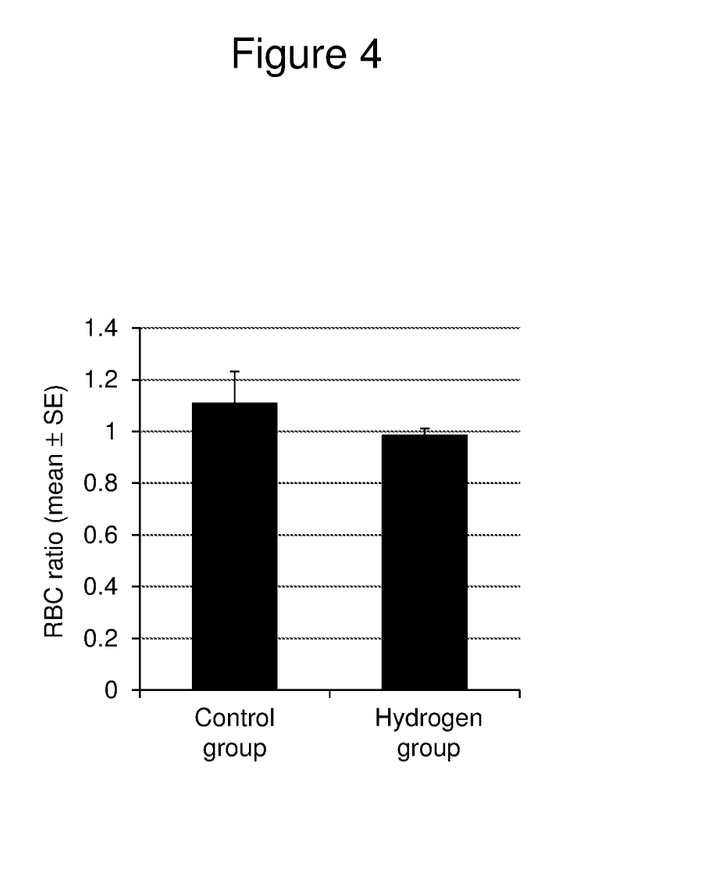
FIG. 4 is a graph showing the mean±standard error (SE) of the relative value of the red blood cell count (RBC) immediately after radiation treatment to the RBC before radiation treatment (the RBC before radiation treatment is taken as 1) in the control group (Control, n=7) and the hydrogen group (H2, n=16), respectively. All ratios are represented by the relative value of the RBC after radiation treatment to the RBC before radiation treatment.

FIG. 4 shows the mean±standard error (SE) of the relative value of the red blood cell count (RBC) immediately after radiation treatment to the RBC before radiation treatment (the RBC before radiation treatment is taken as 1) in the control group (Control, n=7) and the hydrogen group (H2, n=16), respectively. The RBC ratio was 1.108±0.124 in the control group and 0.985±0.027 in the hydrogen group. There was no statistically significant difference between both groups, and the RBC ratio in the hydrogen group was almost the same as that in the control group.

Figure 5:
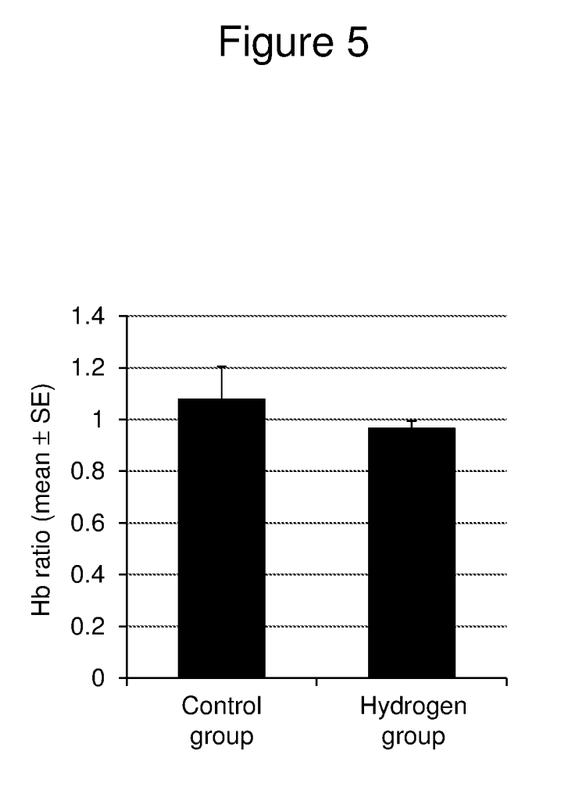
FIG. 5 is a graph showing the mean±standard error (SE) of the relative value of the hemoglobin level (Hb) immediately after radiation treatment to the Hb before radiation treatment (the Hb before radiation treatment is taken as 1) in the control group (Control, n=7) and the hydrogen group (H2, n=16), respectively. All ratios are represented by the relative value of the Hb after radiation treatment to the Hb before radiation treatment.

FIG. 5 shows the mean±standard error (SE) of the relative value of the hemoglobin level (Hb) immediately after radiation treatment to the Hb before radiation treatment (the Hb before radiation treatment is taken as 1) in the control group (Control, n=7) and the hydrogen group (H2, n=16), respectively. The Hb ratio was 1.078±0.126 in the control group and 0.966±0.029 in the hydrogen group. There was no statistically significant difference between both groups, and the Hb ratio in the hydrogen group was almost the same as that in the control group.

Figure 6:
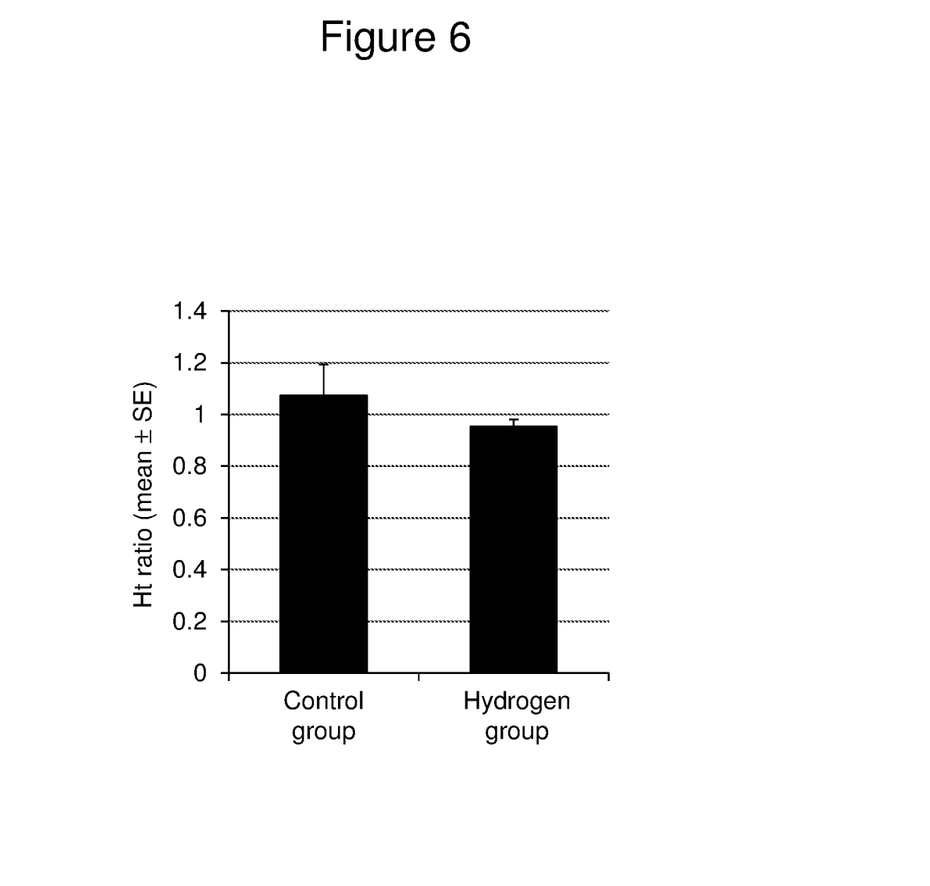
FIG. 6 is a graph showing the mean±standard error (SE) of the relative value of the hematocrit level (Ht) immediately after radiation treatment to the Ht before radiation treatment (the Ht before radiation treatment is taken as 1) in the control group (Control, n=7) and the hydrogen group (H2, n=16), respectively. All ratios are represented by the relative value of the Ht after radiation treatment to the Ht before radiation treatment.

FIG. 6 shows the mean±standard error (SE) of the relative value of the hematocrit level (Ht) immediately after radiation treatment to the Ht before radiation treatment (the Ht before radiation treatment is taken as 1) in the control group (Control, n=7) and the hydrogen group (H2, n=16), respectively. The Ht ratio was 1.073±0.121 in the control group and 0.953±0.027 in the hydrogen group. There was no statistically significant difference between both groups, and the Ht ratio in the hydrogen group was almost the same as that in the control group.

Figure 7:
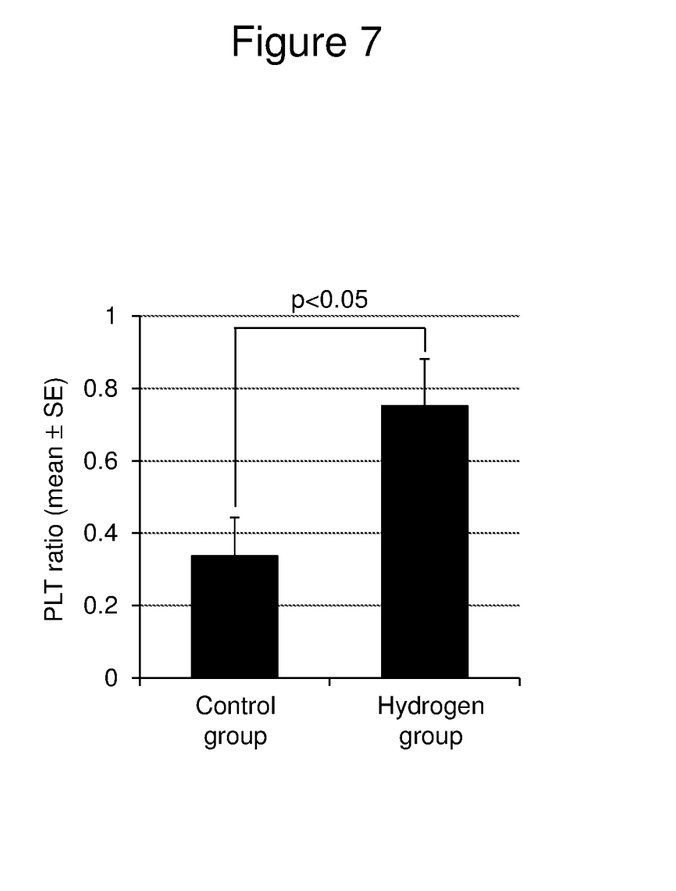
FIG. 7 is a graph showing the mean±standard error (SE) of the relative value of the platelet count (PLT) immediately after radiation treatment to the PLT before radiation treatment (the PLT before radiation treatment is taken as 1) in the control group (Control, n=7) and the hydrogen group (H2, n=16), respectively. All ratios are represented by the relative value of the PLT after radiation treatment to the PLT before radiation treatment.

FIG. 7 shows the mean±standard error (SE) of the relative value of the platelet count (PLT) immediately after radiation treatment to the PLT before radiation treatment (the Ht before radiation treatment is taken as 1) in the control group (Control, n=7) and the hydrogen group (H2, n=16), respectively. The PLT ratio was 0.337±0.106 in the control group and 0.752±0.130 in the hydrogen group. The decrease in the PLT ratio induced by radiation was significantly inhibited in the hydrogen group, compared with that in the control group, and a statistically significant difference (p<0.05) was observed between both groups.

Figure 8:
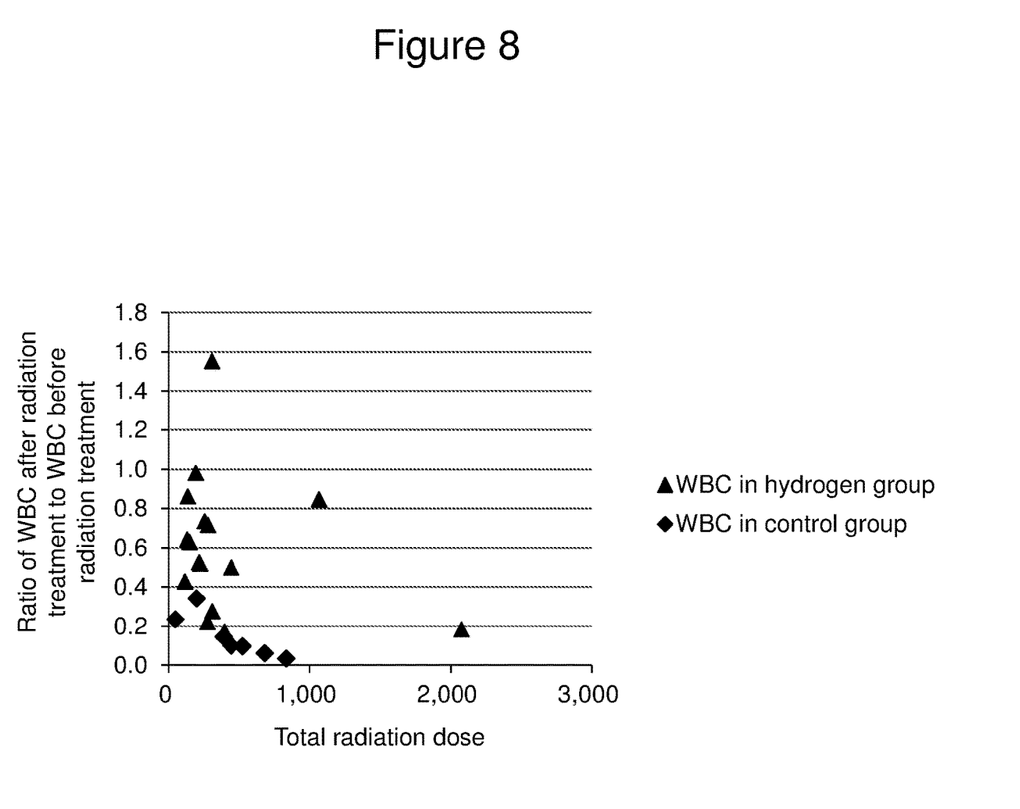
FIG. 8 is a graph showing the correlation between the total radiation dose (horizontal axis) and the relative value (vertical axis) of the white blood cell count (WBC) immediately after radiation treatment to the WBC before radiation treatment (the WBC before radiation treatment is taken as 1) in the control group (black diamond) (Control, n=7) and the hydrogen group (black triangle) (H2, n=16), respectively.

FIG. 8 shows the correlation between the total radiation dose (horizontal axis) and the relative value (vertical axis) of the white blood cell count (WBC) immediately after radiation treatment to the WBC before radiation treatment (the WBC before radiation treatment is taken as 1) in the control group (Control, n=7) and the hydrogen group (H2, n=16), respectively. In the scatter plot, the WBC ratio in the hydrogen group was plotted in a relatively upper area (in the upper direction of the vertical axis), as compared with that in the control group.

Figure 9:
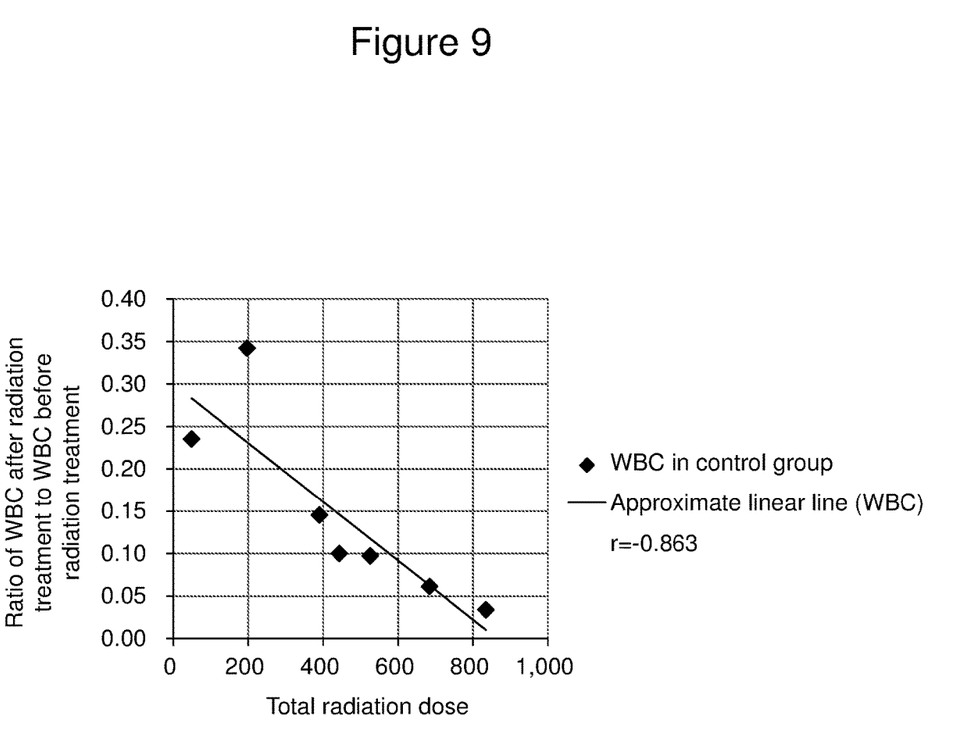
FIG. 9 is a graph which shows in closeup only the data of control group (black diamond) (Control, n=7) from the graph showing the correlation in FIG. 8 and also shows the correlation coefficient.

FIG. 9 is a graph which shows in closeup only the data of control group (Control, n=7) from the graph showing the correlation in FIG. 8 and also shows the correlation coefficient determined therefrom. In the control group, a negative correlation was established between the total radiation dose (horizontal axis) and the relative value (vertical axis) of the white blood cell count (WBC) immediately after radiation treatment to the WBC before radiation treatment (the WBC before radiation treatment is taken as 1), with the correlation coefficient r=−0.863. On the other hand, in the hydrogen group, correlation coefficient r=−0.255 was shown, and no correlation was established.

The above results show as follows.

The inhalation effect of hydrogen gas was markedly observed in the white blood cell count (WBC) and the platelet count (PLT) in peripheral blood which were measurements item susceptible to irradiation. On the other hand, the red blood cell count (RBC), the hemoglobin level (Hb) and the hematocrit level (Ht) were unaffected measurement items because the relative values were approximately 1 even in the control group, and the inhalation of hydrogen gas had no effect on these indicators. It was shown that by the inhalation of hydrogen gas in a hyperbaric capsule, a hyperbaric pressure and the inhalation of hydrogen gas worked synergistically on radiation damage protection.

On the other hand, the correlation between the total radiation dose and the relative value of the white blood cell count (WBC) was established in the control group but not in the hydrogen group. Assuming that the hydrogen gas inhaled in a hyperbaric capsule competitively antagonizes radiation damage, the correlation would be established also in the hydrogen group and the approximate linear line determined the WBC ratio in the control group would parallel shift to the upper side. Therefore, it suggests the possibility that the hydrogen gas inhaled by a cancer patient in the hyperbaric capsule according to the present invention might noncompetitively antagonize radiation damage.

White blood cells (WBCs) are comprised of lymphocytes, granulocytes (neutrophils, eosinophils and basophils) and monocytes, but in the tests in Example 1 above, the influence of irradiation on each fraction of white blood cells (any of lymphocytes, granulocytes and monocytes) and the effect of the inhalation of hydrogen gas in the hyperbaric capsule on the influence was not observed. However, in a broad sense, white blood cells are included in immunocompetent cells responsible for defense mechanisms. Platelets (PLT) play a role in blood coagulation together with coagulation factors present in vascular endothelial cells and plasma, and are also deeply involved in defense reactions such as inflammatory reaction, immune reactions and defenses against infections. Accordingly, the result that the hydrogen gas inhaled by a cancer patient in the hyperbaric capsule according to the present invention was markedly effective against bone marrow damage by radiation, particularly against decreases in the white blood cell count (WBC) platelet count (PLT) suggests that the hydrogen gas inhaled by the cancer patient in the hyperbaric capsule may be effective against cancers and in improving inflammation and deterioration in immune function associated with irradiation. Hydrogen gas has the property of eliminating a reactive oxygen species (ROS) generated by radiation (Zhao S. et al., J. Cell. Mol. Med. 2014; 18 (5): 938-946).

INDUSTRIAL APPLICABILITY

The radiation damage protecting agent comprising hydrogen gas as an active ingredient according to the present invention can treat, alleviate and improve radiation damage such as bone marrow damage in a human patient who has been exposed to radiation or who has received radiotherapy, and can be also expected to have the effect of improving inflammation and deterioration in immune function associated with irradiation.

All publications, patents and patent applications cited herein are incorporated herein by reference in their entirety.

The invention claimed is:

1. A method for treating or alleviating-radiation damage in a human patient who has been exposed to radiation or who has received or receives radiotherapy, comprising inhaling a radiation damage protecting agent comprising hydrogen gas as an active ingredient by the human patient,
   wherein the radiation damage is a decrease in number of white blood cells and/or platelets,
   wherein the radiation damage protecting agent is a gas comprising hydrogen gas at a concentration of 18.5% by volume or less.

2. The method according to claim 1, wherein the concentration of the hydrogen gas is 1% by volume to 10% by volume.

3. The method according to claim 1, wherein the radiation damage protecting agent comprising hydrogen gas is inhaled transpulmonarily to the human patient.

4. The method according to claim 1, wherein the human patient is a cancer patient.

* * * * *